US012558196B2

(12) United States Patent
Ruetze et al.

(10) Patent No.: US 12,558,196 B2
(45) Date of Patent: Feb. 24, 2026

(54) DENTAL DEVICE FOR RIDGE PRESERVATION AND PROMOTION OF JAW BONE REGENERATION IN AN EXTRACTION SITE

(71) Applicants: DENTSPLY SIRONA Inc., York, PA (US); SIRONA DENTAL SYSTEMS GMBH, Bensheim (DE)

(72) Inventors: Martin Ruetze, Mannheim (DE); Naim Karazivan, Quebec (CA)

(73) Assignee: Dentsply Sirona Inc., York, PA (US)

( * ) Notice: Subject to any disclaimer, the term of this patent is extended or adjusted under 35 U.S.C. 154(b) by 906 days.

(21) Appl. No.: 17/432,509

(22) PCT Filed: Feb. 14, 2020

(86) PCT No.: PCT/EP2020/053914
§ 371 (c)(1),
(2) Date: Aug. 20, 2021

(87) PCT Pub. No.: WO2020/169475
PCT Pub. Date: Aug. 27, 2020

(65) Prior Publication Data
US 2022/0151740 A1 May 19, 2022

(30) Foreign Application Priority Data
Feb. 21, 2019 (EP) ..................................... 19020081

(51) Int. Cl.
*A61C 8/02* (2006.01)
*A61C 8/00* (2006.01)
*A61K 38/18* (2006.01)
*A61L 31/02* (2006.01)
*A61L 31/14* (2006.01)

(52) U.S. Cl.
CPC .......... *A61C 8/0006* (2013.01); *A61C 8/0013* (2013.01); *A61C 8/0016* (2013.01); *A61C 8/0022* (2013.01); *A61C 8/0024* (2013.01); *A61K 38/18* (2013.01); *A61L 31/148* (2013.01); *A61C 8/0039* (2013.01); *A61L 31/022* (2013.01); *A61L 2300/406* (2013.01); *A61L 2300/414* (2013.01)

(58) Field of Classification Search
None
See application file for complete search history.

(56) References Cited
U.S. PATENT DOCUMENTS

| | | | |
|---|---|---|---|
| 5,957,690 A | 9/1999 | Bartee et al. | |
| 2004/0209228 A1 | 10/2004 | Ilan | |
| 2017/0014169 A1* | 1/2017 | Dean .................. | A61B 17/8071 |
| 2020/0000558 A1* | 1/2020 | Hansson .............. | A61C 8/0018 |

FOREIGN PATENT DOCUMENTS

| | | | |
|---|---|---|---|
| CA | 3138474 | 8/2020 | |
| DE | 19713305 A1 * | 10/1998 | .......... A61C 8/0006 |
| DE | 102005039382 A1 * | 2/2007 | ......... A61B 17/8071 |
| EP | 0131831 A2 * | 1/1985 | |
| EP | 3698750 A1 | 8/2020 | |
| EP | 3927277 A1 | 12/2021 | |
| JP | S6085739 | 5/1985 | |
| JP | 2014113592 A | 6/2014 | |
| JP | 2022521304 A | 4/2022 | |
| JP | 7597721 B2 | 12/2024 | |
| KR | 20170071015 | 6/2017 | |
| KR | 102778865 B1 | 3/2025 | |
| WO | 2007086832 A2 | 8/2007 | |
| WO | WO-2009118725 A1 * | 10/2009 | .......... A61C 8/0006 |
| WO | 2016134797 | 9/2016 | |
| WO | WO-2020169475 A1 | 8/2020 | |

OTHER PUBLICATIONS

Machine translation (2024) of Engelke (DE 19713305 A1, Description).*
Description of DE 10 2005 039 382 A1, Machine translation (2025).*
International Search Report; PCT/EP2020/053914; Apr. 20, 2020 (completed); Apr. 30, 2020 (mailed).
Written Opinion of the International Searching Authority; PCT/EP2020/053914; Apr. 20, 2020 (completed); Apr. 30, 2020 (mailed).
International Preliminary Report on Patentability; PCT/EP2020/053914; Apr. 20, 2020 (completed); Apr. 30, 2020 (mailed).
Cochran et.al.; "Bone response to unloaded and loaded titanium implants with a Sandblasted and Acid-Etched surface: A Histometric Study in the Canine Mandible"; Journal of Biomedical Materials Research; vol. 40; pp. 1-11; Jan. 1998.
"Canadian Application Serial No. 3,138,474, Examiners Rule 86(2) Report mailed Jan. 31, 2025", 4 pgs.
"Canadian Application Serial No. 3,138,474, Response filed May 26, 2025 to Examiners Rule 86(2) Report mailed Jan. 31, 2025", 11 pgs.

(Continued)

*Primary Examiner* — H. Sarah Park
(74) *Attorney, Agent, or Firm* — SCHWEGMAN LUNDBERG & WOESSNER, P.A.

(57) ABSTRACT

Dental device (1) for ridge preservation around the socket (2) of an extracted tooth and for promoting jaw bone regeneration inside the socket (2) of the extracted tooth, the dental device (1) comprising: a screw (3) which is entirely made of a biodegradable material to eliminate the need for a removal surgery, wherein the screw (3) is adapted for tight fixation within the jaw bone (4) in the socket (2) to prevent micromovements during bone-tissue regeneration, wherein the screw (2) has a length such that its top is, in the inserted state, flush with the alveolar ridge (5) around the socket (2) to promote full bone regeneration inside the socket (2), and wherein the screw (3) has a hollow (6) and pores (7), wherein the diameters of the pore (7) is substantially equal to or larger than 20 micrometers.

15 Claims, 2 Drawing Sheets

(56) References Cited

OTHER PUBLICATIONS

"European Application Serial No. 20704042.9, Response Filed Apr. 16, 2025 to Communication lunder Rule 71(3) EPC mailed Dec. 17, 2025", 5 pgs.
"European Application Serial No. 19020081.6, Extended European Search Report mailed Aug. 27, 2019", 8 pgs.
"European Application Serial No. 19020081.6, Noting of loss of rights pursuant to Rule 112(1) EPC mailed Mar. 23, 2021", 2 pgs.
"European Application Serial No. 20704042.9, Communication Pursuant to Article 94(3) EPC mailed Jan. 31, 2024", 4 pgs.
"European Application Serial No. 20704042.9, Communication Pursuant to Article 94(3) EPC mailed Feb. 2, 2023", 4 pgs.

"European Application Serial No. 20704042.9, Response filed May 8, 2024 to Communication Pursuant to Article 94(3) EPC mailed Jan. 31, 2024", 12 pgs.
"European Application Serial No. 20704042.9, Response filed May 31, 2023 to Communication Pursuant to Article 94(3) EPC mailed Feb. 2, 2023", 10 pgs.
"Japanese Application Serial No. 2021-549326, Notification of Reasons for Refusal mailed Jan. 9, 2024", w/ English Translation, 6 pgs.
"Japanese Application Serial No. 2021-549326, Office Action mailed Jan. 16, 2024", w/ English translation, 6 pgs.
"Japanese Application Serial No. 2021-549326, Office Action mailed Aug. 31, 2023", W/English Translation, 8 pgs.
"Japanese Application Serial No. 2021-549326, Office Action mailed Sep. 5, 2023", w/ English translation, 8 pgs.

* cited by examiner

DENTAL DEVICE FOR RIDGE PRESERVATION AND PROMOTION OF JAW BONE REGENERATION IN AN EXTRACTION SITE

TECHNICAL FIELD OF THE INVENTION

The present invention relates to dental techniques for ridge preservation and promotion of jaw bone regeneration in extraction sites prior to an implantation. The present invention more particularly relates to dental devices for ridge preservation around the socket of an extracted tooth and for promoting the jaw bone regeneration inside the socket of the extracted tooth prior to an implantation.

BACKGROUND ART OF THE INVENTION

The immediate placement of dental implants into fresh extraction sockets is often disadvised as comparatively higher implant failure rates are observed in comparison to a successive socket healing and implantation procedure. An associated problem with this successive procedure is that the alveolar ridge surrounding the extraction socket is massively resorbed during the healing time. In the worst-case scenario, the remaining bone volume is insufficient to place an implant. For this reason, several ridge preservation techniques were proposed and developed to decrease jaw bone resorption. A wide range of ridge preservation techniques, such as socket filling with graft materials, collagen plugs and coverage with various membranes or gingiva punches were shown to be effective, however only to a limited extent. In these ridge preservation techniques, lateral (buccolingual) thinning of 2 to 3 mm and a loss of 1 to 2 mm vertical height cannot be prevented. These techniques all lack the effectiveness to preserve the original shape of the jaw. Thus, the dental clinical research community judges full ridge preservation as impossible.

WO 2016/134797 discloses a ridge preservation technique wherein a bone defect in the jaw bone is filled with bone graft material and covered with a bioresorbable magnesium membrane, and wherein the bioresorbable membrane is fixed to the jaw bone with pins, nails or screws made from a magnesium alloy. In such commonly known techniques of merely filling the defect with a particulate or moldable biomaterial and placing a bioresorbable membrane, it is likely that vertical collapses occur. Moreover, non-stabilized graft materials are subject to displacement upon exposure to chewing forces. It is also known that micromovement of the substrate during tissue regeneration favors the growth of soft tissue versus new bone tissue. Furthermore, poor nutrient perfusion within bone graft material is especially observed with dense putties. The commonly known ridge preservation techniques provide limited blood supply and consequently slow bone growth during the healing phase.

DISCLOSURE OF THE INVENTION

An objective of the present invention is to overcome the disadvantages of the prior art in an effective way and to provide a dental device for ridge preservation and promotion of jaw bone regeneration in an extraction site.

This objective is achieved by the dental device as defined in claim 1. The dependent claims define further developments which have been achieved through the present invention.

According to the present invention the dental device has a screw that is entirely made of a biodegradable material to eliminate the need for a removal surgery. The screw is adapted for tight fixation within the jaw bone in the socket to prevent micromovements during bone tissue regeneration. The screw has a length such that its top, in the inserted state, is at the same level with the alveolar ridge around the socket to promote full bone regeneration inside the socket. And the screw has a hollow and pores to allow blood perfusion into the hollow for the formation of blood coagulum to serve as a biological matrix for bone growth inside the socket.

The dental device of the present invention provides an effective technique for ridge preservation and promotion of jaw bone regeneration in an extraction site. Since the screw is manufactured from a biodegradable material, it achieves a significant advantage over previous experimental approaches with titanium ceramic material that would need to remain in the patient for lifetime and would have caused a bad perception by the costumer and raised the concern of particle generation when drilling through the titanium ceramic material needed for implant placement. Since the dental device can be tightly inserted like a screw into the socket, it provides increased stability to the defect site during tissue regeneration and prevents the growth of soft tissue versus new bone tissue. In this respect, the screw provides an additional advantage in comparison to non-stabilized graft materials which are subject to displacement upon exposure to chewing forces. Since the screw serves as a post to maintain the height of the alveolar ridge, no vertical collapse will occur, the alveolar geometry of the baseline situation is maintained, the loss of bone height is prevented, and the original shape of the jaw can be preserved. This benefit is also of value in comparison with approaches where graft materials are used to underfill the membrane as graft material resorption still leads to a loss of vertical height. Since the screw has a hollow and pores, it allows blood perfusion and intimate connection to the blood clot and subsequent promotion of bone regeneration.

According to the present invention, to cover various anatomical cases corresponding to different socket depths and sizes, the screw of the dental device may be provided in different predetermined lengths and diameters to allow adjustment to the individual socket depths and sizes respectively. Thereby, the dentist can select and apply the dental device in accordance with the need of the patient.

According to the present invention, the dental device may be manufactured from any type of resorbable material offering the appropriate mechanical properties. For example, biodegradable metals and/or biodegradable polymers may be used.

According to the present invention, different parts of the screw may be manufactured from biodegradable materials with different composition and density. Thereby the resorption rates throughout the screw can be adjusted to achieve uniform healing inside the socket. Thereby, also the mechanical strength can be adjusted throughout the screw.

According to the present invention, the dental device may be manufactured from magnesium or a magnesium alloy. In this respect, an advantageous effect is achieved as the degradation of the screw leads to deliberation of osteopromotive magnesium ions. It is well-known that magnesium triggers molecular pathways for new bone formation and that magnesium can increase the performance of calcium phosphate bone graft materials in vivo. Thus, the present invention provides the best-known bone formation environment, and a biological stimulus.

According to the present invention, aside from magnesium, other bone formation promoting elements such as strontium may be included into the biodegradable magnesium alloy.

According to the present invention, the screw, particularly the surface of the screw may be enriched with antibiotic agents or growth factors which promote bone formation.

According to the present invention, the threads of the screw may be formed into the apical end to allow adjustment of the level of the distal end to match the height of the alveolar ridge during insertion. The threads of the screw of the dental device serve for tight fixation within the socket either in a self-tapping or pre-tapping manner. The threads are provided preferably only at the tapering apical end of the screw as the screw has preferably a smaller width than the socket that secures some space for the blood coagulum.

According to the present invention a flat surface is formed on the top of the screw to serve as an underlay for a separate dental barrier membrane. Alternatively, the flat surface may be formed with a size and shape large enough to cover the socket itself to serve as a barrier. The flat surface is substantially equal to or larger than the outer diameter of the screw so as to cover the entire socket including the space between the screw and the socket. The flat surface may have different predetermined sizes and shapes to cover all anatomical cases corresponding to different socket sizes and shapes respectively. Herein any dental barrier membrane commonly known to those skilled in the art can be used with the dental device. The dental barrier membrane may be further fixed in place through the gingival flaps around the socket. Similarly, the flat surface of the screw can be covered with the gingival flaps around the socket.

According to the present invention, the dental device is an integral piece wherein the flat surface and the screw including the hollow and the pores are formed from one or more biodegradable materials. The dental device is preferably manufactured partly or entirely through an additive manufacturing method, preferably through the selective laser melting method.

According to the present invention, the screw may have a uniform grid like structure, a scaffold like structure or a perforated structure surrounding the hollow to form the pores. The size of the pores should be relatively small to improve mechanical strength; however, the pores must also be sufficiently large to allow blood perfusion into the hollow. Herein, the pores each may have a size of preferably 0.005 to 3 millimeters, more preferably at least 20 micrometers, even more preferably at least 30 micrometers, or even more preferably at least 60 micrometers, and even more preferably less than 500 micrometers.

According to the present invention, the screw may have an opening in the apical end to allow blood perfusion from the jaw bone into the hollow whereas the distal end of the screw, particularly the flat surface is preferably closed to prevent intrusion of soft tissue, or impurities and the like into the hollow.

BRIEF DESCRIPTION OF THE DRAWINGS

In the subsequent description, the present invention will be described in more detail by using exemplary embodiments and by referring to the drawings, wherein FIG. 1—is a schematic perspective cutaway view of a tooth extraction site into which a dental device according to an embodiment of the present invention has been inserted.

Figure 1:
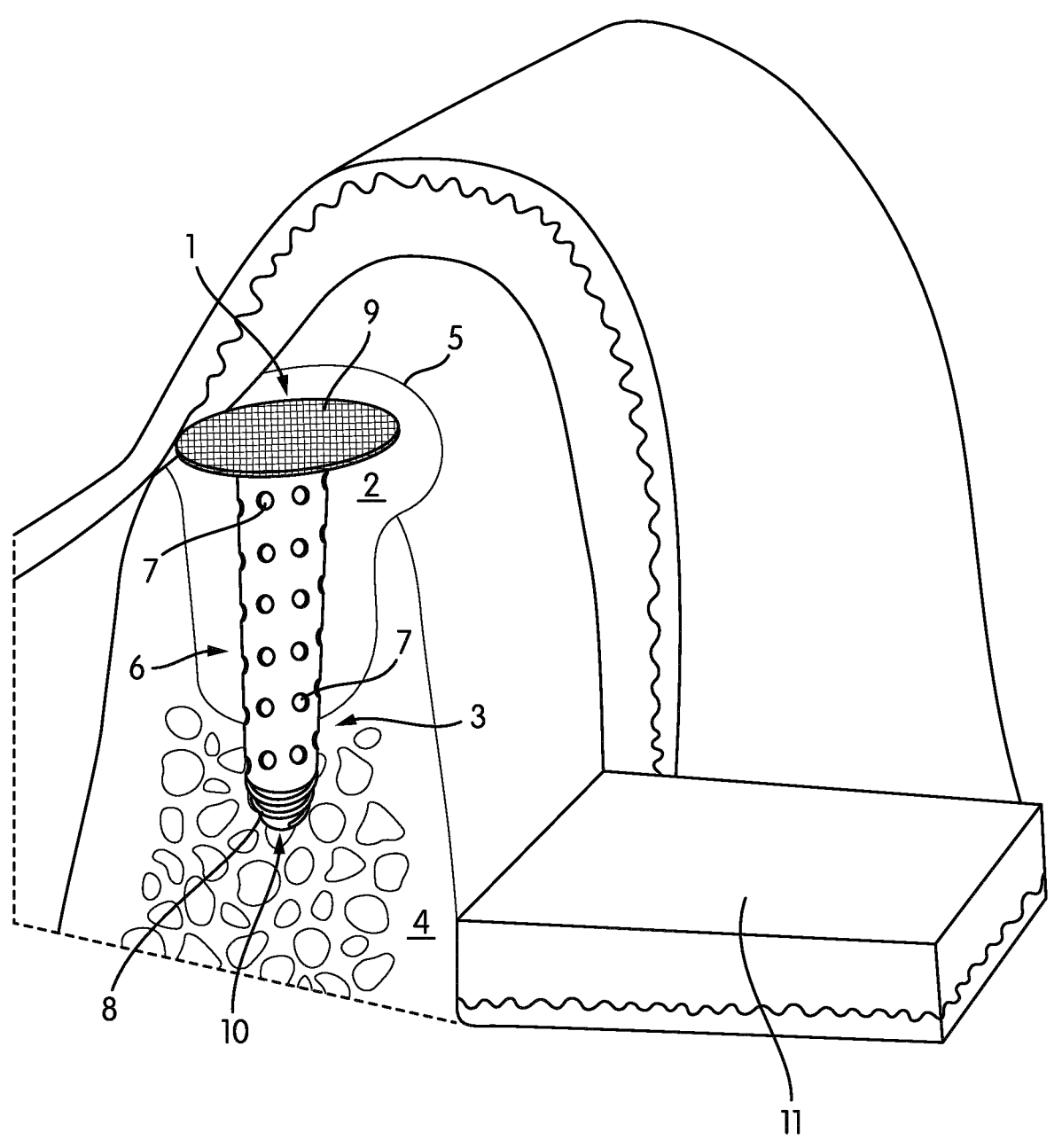

The reference numbers shown in the drawings denote the elements as listed below and will be referred to in the subsequent description of the exemplary embodiments.

1. Dental device
2. Socket
3. Screw
4. Jaw bone
5. Alveolar ridge
6. Hollow
7. Pore
8. Thread
9. Flat surface
10. Opening
11. Gingival flap FIG. 1 shows a dental device (1) for ridge preservation around the socket (2) of an extracted tooth and for promoting jaw bone regeneration inside the socket (2) of the extracted tooth according to an embodiment of the present invention. The dental device (1) has a screw (3) which is entirely made of a biodegradable material. The screw (3) is adapted for tight fixation within the jaw bone (4) in the socket (2). The screw (3) has a length such that its top, in the inserted state, is flush with the alveolar ridge (5) around the socket (2). The screw (3) has a hollow (6) and pores (7) to allow blood perfusion into the hollow (6). The diameter of the pore (7) is preferably substantially equal to or larger than 20 micrometers, more preferably substantially equal to or larger than 30 micrometers, or even more preferably substantially equal to or larger than 60 micrometers. The diameter of the pore (7) is preferably substantially smaller than 500 micrometers.

In alternative versions of this embodiment (not shown), the screws (3) have different predetermined lengths and diameters to cover all anatomical cases corresponding to different socket (2) depths and sizes respectively.

The biodegradable material is preferably polymer-based and/or metal-based. The biodegradable material preferably includes magnesium and/or strontium. The biodegradable material may also include growth factors and/or antibiotic agents within or on the surface of the screw (3). Different parts of the screw (3) may be manufactured from biodegradable materials with different composition and/or density.

In this embodiment, the threads (8) of the screw (3) are adapted for pre-tapping. Alternatively, the threads (8) of the screw (3) may be adapted for self-tapping. The threads (8) are provided preferably only at the tapering apical end of the screw (3).

Figure 2:
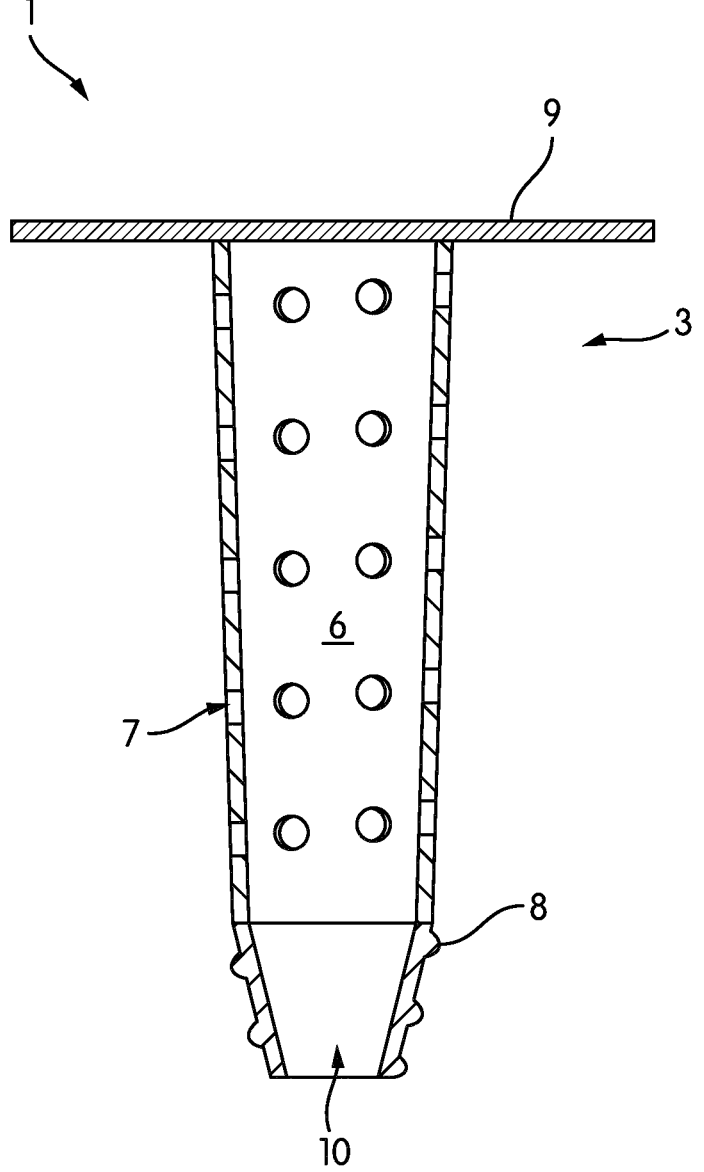
FIG. 2—is a schematic cross-sectional view of the dental device according to the embodiment of the present invention.

FIG. 2 shows a cross sectional view of the dental device (1) of FIG. 1. As shown in FIG. 2 the dental device (1) has a flat surface (9) formed onto the top of the screw (3), which can serve as barrier itself or as a support for a dental barrier membrane. The flat surface (9) is equal to or substantially larger than the outer diameter of the screw (3) so as to cover the entire socket (2). The dental barrier membrane is used for covering the socket (2). The dental barrier membrane is provided separately from the flat surface (9). The flat surface (9) has a size and shape adapted to support the dental barrier membrane like an underlay.

In alternative versions of this embodiment, the flat surfaces (9) have different predetermined sizes and shapes to cover all anatomical cases corresponding to different socket (2) sizes and shapes respectively.

As shown in FIG. 2, the flat surface (9) and the screw (3) including the hollow (6) and the pores (7) are provided as an integral piece from the biodegradable material(s), preferably from a magnesium alloy. The dental device (1) is preferably manufactured partly or entirely through an additive manufacturing method. The additive manufacturing method preferably comprises the selective laser melting method applied to the above mentioned biodegradable material in powder form. The pores (7) are formed with the preferred diameters or sizes during the additive manufacturing process through selective laser melting of the biodegradable material.

A shown in FIG. 2, the screw (3) has a perforated structure surrounding the hollow (6). The perforated structure forms the pores (7) in the screw (3) for blood perfusion. Alternately, a grid like or scaffold like structure may be manufactured to form the pores (7) in the screw (3) for blood perfusion.

A shown in FIG. 2, the screw (3) has an opening (10) in the apical end to allow blood perfusion from the jaw bone (4) into the hollow (6). And the screw (3) is closed on the distal end to prevent intrusion of soft tissue and the like into the hollow (6).

The dental device (1) can be used in fresh extractions sites prior to an implantation. The dentist determines the depth, size and shape of the socket (2) and selects a dental device (1) with the correctly matching length, diameter, size and shape. Thereafter the screw (3) is inserted into the socket (2) such that the upper end is at the same level with the alveolar ridge (5). Next a dental barrier membrane is optionally placed on the flat surface (9) and fixed in place by the gingival flaps (11) in the surrounding gingiva. The gingival flap (11) is joined with sutures. When the extraction site is healed, the dental device (1) is completely resorbed and no removal surgery is necessary. Thereafter an implant can be inserted into the regenerated jaw bone. With the present invention the implant failure rate can be significantly reduced.

The invention claimed is:

1. A dental device (1) for ridge preservation around the socket (2) of an extracted tooth and for promoting jaw bone regeneration inside the socket (2) of the extracted tooth, the dental device (1) comprising:
    a screw (3) which is entirely made of a biodegradable material to eliminate the need for a removal surgery;
    wherein the screw (3) is adapted for tight fixation within the jaw bone (4) in the socket (2) to prevent micromovements during bone-tissue regeneration;
    a flat surface (9) integrally formed with the top of the screw (3), wherein the flat surface (9) is larger than the outer diameter of the screw (3) so as to cover the space between the socket (2) and the screw (3);
    wherein the screw (3) has a tapering apical end and a length such that its top is, in the inserted state, at the same level with the alveolar ridge (5) around the socket (2) to promote full bone regeneration inside the socket (2);

wherein the screw (3) is provided with threads (8) only at the tapering apical end, and wherein the screw (3) includes an opening (10) in the apical end to allow blood perfusion from the jaw bone (4);
    wherein the screw (3) has a hollow (6) and pores (7) to allow blood perfusion into the hollow (6) for the formation of blood coagulum to serve as biological matrix for bone growth inside the socket (2), and
    wherein the diameter of one or more pores (7) is each equal to or larger than 20 micrometers.

2. The dental device (1) according to claim 1, wherein the diameter of the pore (7) is equal to or larger than 60 micrometers.

3. The dental device (1) according to claim 1, wherein the diameter of the pore (7) is smaller than 500 micrometers.

4. The dental device (1) according to claim 1, wherein the screw (3) is provided in varying lengths and/or diameters to accommodate varying socket (2) depths and sizes.

5. The dental device (1) according to claim 1, wherein the biodegradable material is polymer-based and/or metal-based.

6. The dental device (1) according to claim 5, wherein the biodegradable material comprises magnesium.

7. The dental device (1) according to claim 5, wherein the biodegradable material comprises strontium.

8. The dental device (1) according to claim 1, wherein the biodegradable material comprises growth factors and/or antibiotic agents.

9. The dental device (1) according to claim 8, wherein the growth factors and/or antibiotic agents are deposited on the surface of the screw (3).

10. The dental device (1) according to claim 9, wherein the threads (8) of the screw (3) are adapted for self-tapping.

11. The dental device (1) according to claim 9, wherein the threads (8) of the screw (3) are adapted for pre-tapping.

12. The dental device (1) according to claim 1, further comprising:
    a dental barrier membrane for covering the socket (2) wherein the flat surface (9) has a size and shape adapted to support the dental barrier membrane from below, wherein the dental barrier membrane is provided separately from the flat surface (9).

13. The dental device (1) according to claims 1, wherein the dental device (1) has been manufactured partly or entirely through an additive manufacturing method.

14. The dental device (1) according to claim 13, wherein the additive manufacturing method comprises a selective laser melting method.

15. The dental device (1) according to claim 1, wherein the screw (3) has a grid and/or a scaffold structure surrounding the hollow (6) and defining the pores.

* * * * *